United States Patent [19]

Morley

[11] 4,339,621

[45] Jul. 13, 1982

[54] PREPARATION OF O-BENZYL TOLUENE

[75] Inventor: John O. Morley, Rochdale, England

[73] Assignee: Imperial Chemical Industries Limited, London, England

[21] Appl. No.: 237,774

[22] Filed: Feb. 24, 1981

[30] Foreign Application Priority Data

Mar. 27, 1980 [GB] United Kingdom ............... 8010243

[51] Int. Cl.$^3$ .................... C07C 2/02; C07C 6/12; C07C 13/28; C07C 15/16
[52] U.S. Cl. .................................... 585/422; 585/426
[58] Field of Search ........................... 585/422, 426

[56] References Cited

U.S. PATENT DOCUMENTS

| 3,000,985 | 9/1961 | Schmerling | 585/426 |
| 3,799,991 | 3/1974 | Smith | 585/426 X |
| 4,049,733 | 9/1977 | Martan | 585/426 |
| 4,117,019 | 12/1977 | Eilingsfeld | 585/422 X |

FOREIGN PATENT DOCUMENTS 48-40754 6/1973 Japan.
49-75563 7/1974 Japan.

Primary Examiner—Paul F. Shaver
Attorney, Agent, or Firm—Cushman, Darby & Cushman

[57] ABSTRACT

A process for the preparation of diphenylmethanes and especially of unsubstituted and alkyl substituted diphenylmethanes such as diphenylmethane (DPM) itself and 2-benzyl toluene (OBT) which is an intermediate in the preparation of anthraquinone.

The process involves the reaction of a benzene with an α-chloromethyl benzene in the presence of sulphuric acid and a cationic surfactant, such as a long chain quaternary ammonium salt, or a non-ionic surfactant susceptible to protonation under strong acid conditions, such as an alkoxylated alkyl phenol.

10 Claims, No Drawings

PREPARATION OF O-BENZYL TOLUENE

This invention relates to a process for the preparation of diphenylmethanes and especially of unsubstituted and alkyl substituted diphenylmethanes such as diphenylmethane (DPM) itself and 2-benzyl toluene (OBT) which is an intermediate in the preparation of anthraquinone.

Diphenylmethanes are conveniently prepared by the reaction of α-chloromethylbenzenes with benzenes in the presence of a dehydrohalogenation catalyst. A number of different catalysts, including zinc, aluminium chloride, copper chromite and sulphuric acid, have been proposed for this purpose but none of these, with the exception of sulphuric acid, has proved to be of commercial importance either on cost grounds or because it also promotes side reactions to unwanted products, usually isomers, which are difficult to separate from the desired product. Even sulphuric acid has disadvantages because at very high strengths (approaching 100%) sulphonation, particularly of substituted benzenes, sets in at a significant rate and the acid is not miscible with the reactants. It does however have the great merit of low cost compared with the alternative catalysts and it is also generally less toxic.

In Japanese Patent Specifications Nos. 48-40754 and 49-75563 (Toyama) it is proposed to prepare OBT by reaction between 2-chloromethyl-toluene (2-CMT) and benzene using sulphuric acid as catalyst, with a molar ratio for benzene to 2-CMT of at least 7:1 in order to inhibit sulphonation of OBT and 2-CMT and to reduce the tendency for 2-CMT to condense with itself or OBT rather than with benzene. Although the reported yields are very high, above 90% based on 2-CMT, the reaction is very slow; a batch involving about 1 gram mole of 2-CMT took about 5 hours to completion.

In U.S. Pat. No. 4,117,019 (BASF) it has been proposed to imporve the contact between 2-CMT, benzene and the catalyst (sulphuric acid, phosphoric acid and/or organic sulphonic acids) by performing the reaction under conditions of high shear. It is stated that the high shear may be provided by high speed agitation, above 700 rpm and preferably 800 to 2000 rpm, or by the use of high shear energy mixing equipment, such as homogenisers, cascades, recirculation loops etc. Under such mixing conditions it is stated that the reactants become more intimately mixed so that emulsions of the two phases are formed in which the droplets are preferably less than 1000 nanometers, and it was found that the molar ratio of benzene to 2-CMT could be reduced below 7:1 without any significant increase in side reactions. However, even using improved agitation, a reaction at the ½ gram mole scale (2-CMT) is reported to take about 5 hours to completion and a reaction at the 8 gram mole scale, using a recirculation loop, is reported to take 3½ hours.

It is believed that the reaction rates would be even lower at a reasonable commercial scale of operation say 100 to 1000 kilograms per hour, when efficient mixing is even more difficult to achieve. Furthermore the use of high shear mixing equipment which will withstand the corrosive conditions experienced during the present process would greatly increase the capital cost of manufacturing plant.

The present invention provides means for improving the contact between the α-chloromethylbenzene, the benzene and the catalyst, without the need for special mixing equipment, so that the reaction is completed in a much shorter time, even at a commercial scale of operation, the tendency for side reactions and decompositions is reduced and productivity is increased.

According to the present invention there is provided a process for the preparation of a diphenylmethane by the reaction of a benzene with an α-chloromethyl benzene in the presence of sulphuric acid and a cationic surfactant or a non-ionic surfactant which is susceptible to protonation under strong acid conditions.

The molar proportion of the benzene in the process may be varied from 2:1 to 30:1 in relation to the α-chloromethyl benzene although it preferably varies from 5:1 to 15:1 with respect to the α-chloromethylbenzene.

The benzene and the α-chloromethylbenzene may carry other substituents provided that these are substantially inert under the reaction conditions, e.g. lower ($C_1$ to $C_4$) alkyl, and provided that there is at least one free hydrogen on the benzene which is neither sterically hindered nor deactivated to such an extent as to prevent reaction with the α-chloromethylbenzene. It is preferred that the benzene is unsubstituted and that the α-chloromethylbenzene is α-chloromethylbenzene (α-CMB) itself, or a lower ($C_1$ to $C_4$) alkyl substituted chloromethylbenzene, especially 2-chloromethyltoluene (2-CMT) or 4-chloromethyltoluene (4-CMT).

It is preferred that the sulphuric acid is at least 75% in strength and not more than 100% and more preferably is from 80 to 95%. At concentrations below 80% the rate of reaction tends to fall, especially if the molar ratio of acid to the α-chloromethylbenzene is below 3:1, although this tendency can be reversed by increasing the proportion of acid. At acid strengths above 95% the yield of the diphenylmethane deteriorates progressively presumably because of the progressive increase in the rate of sulphonation of this and the α-chloromethylbenzene.

The quantity of sulphuric acid in the reaction may be varied within wide limits which to some extent depend upon the strength of the sulphuric acid used. Molar proportions in the range from 0.5:1 to 20:1 relative to the α-chloromethylbenzene are generally satisfactory although on cost grounds and to avoid undue batch size it is generally preferred to operate with a molar ratio from 1:1 up to 6:1 when the acid strength is above 80%. With acid strengths below this level it can be advantageous to raise the molar proportion of acid.

Suitable cationic surfactants include phase transfer catalysts containing a quaternary ammonium or phosphonium ion and particularly those in which this ion carries a long aliphatic chain containing from 8 to 25 carbon atoms and preferably from 8 to 20 carbon atoms, such as an alkyl chain. Examples of such surfactants are alkylammonium salts such as tetramethyl ammonium bisulphate, tetrabutyl ammonium chloride and particularly long chain alkylammonium salts such as cetyltrimethylammonium bromide and cetylpyridinium bromide.

The non-ionic surfactants suitable for use in the present invention are capable of accepting a proton in a strong acid medium so that they become cationic species and it is believed that they operate in the same manner as the cationic surfactants in the present process. Anionic surfactants do not appear to promote the reaction. Preferred non-ionic surfactants are poly (lower alkoxy) compounds having aliphatic chains containing from 8 to 25 carbon atoms and more preferably from 8 to 20 carbon atoms, especially alkyl chains. The polyalkoxy chains preferably contain up to 30 alkoxy groups. Examples of suitable non-ionic surfactants are alkoxylated alkyl phenols such as 4-octyl and 4- nonyl phenols in which the aromatic OH group carries a chain of from 8 to 30 ethyleneoxy groups.

The quantity of the surfactant used in the present process is preferably from 0.1 to 5% by weight, based on the weight of the α-chloromethylbenzene and more especially from 0.5% to 2.5%. There is little technical advantage in the use of more than 5% and, although the surfactant may produce an improvement in rate down to the level of 0.1%, the improvement begins to fall off significantly below 0.5% and it is generally preferred to use about 1% of the surfactant.

The rate of reaction in the present process, using 2-CMT and benzene to prepare OBT, is much less dependent upon scale than the equivalent process performed according to Toyama or BASF without any surfactant and the reaction period is much the same on the 1 gram mole scale as on the 100 gram mole scale. Furthermore the yield of OBT, based on 2-CMT usage, is about the same as is obtained under these prior art conditions although the yields reported in these earlier publications could not be achieved by the present applicants. For example, using typical "BASF" conditions, i.e. a molar ratio of benzene to 2-CMT of 6:1, the yield and reaction time at the 1-2 gram mole scale, without surfactant are about 85% and 6 hours respectively, while with surfactant (cetyltrimethylammonium bromide) the yield remains at about 85% but the reaction time falls to 2 hours. Under typical "Toyama" conditions, i.e. a molar ratio of benzene to 2-CMT of 10:1, and on a similar scale the yield and reaction time are, without surfactant, about 85% and 4–5 hours whereas with surfactant the yield remains the same but the reaction time falls to 2 hours.

Although phase transfer catalysts are known to promote reactions which take place, or are catalysed, across a phase boundary they have only generally been used in alkaline systems and the applicants are not aware of any prior disclosure of the use of these agents or of non-ionic surfactants in the promotion of reactions taking place in strongly acidic conditions. It is therefore surprising that the rate of reaction between a benzene and an α-chloromethylbenzene, catalysed by concentrated sulphuric acid, is so effectively promoted by these surfactants.

The process is preferably operated at an elevated temperature in the range from 50° to 120° C. although to avoid the use of high pressure equipment it is preferred to operate in the range 65° C. to 95° C. At the higher acid strengths (above 95%), however, the process can be operated in a reasonable time at lower temperatures down to ambient and these are preferred in order to avoid excessive sulphonation.

The invention is further illustrated by the following specific Examples and Comparative Examples in which all percentages are by weight unless otherwise indicated. The same basic procedure is followed in all the Examples and this is set out below, in general terms, with an indication of any variations. The precise conditions and results for each preparation are summarised in the Table.

GENERAL PROCEDURE

2-CMT is added to a mixture of benzene, sulphuric acid and the surfactant, in a suitable size of reaction vessel fitted with agitator and heating means, at the appropriate reaction temperature and the reaction mixture held at this temperature until reaction is complete, as indicated by the cessation of evolution of hydrogen chloride. The reaction mixture is then cooled to ambient and water (twice the weight of acid used) is added and mixed in thoroughly. The mixture is then allowed to stand and the bottom layer (acid) is removed, washed with benzene (for 0.2 gram mole scale reactions only) and the washings added to the organic phase. The organic phase is washed with water and neutralised with a 10% aqueous solution of sodium hydroxide. Benzene is removed from the neutralised organic phase by distillation at atmospheric pressure and the product, OBT, recovered by distillation under vacuum (4–6 torr).

VARIATIONS

In Examples 1 to 4 the scale is so small that the addition time for 2-CMT is insignificant compared with the reaction period and is included in the total reaction time recorded.

In some cases, the addition of wash water to the organic phase, after it had been separated from the acid, caused the formation of an emulsion but this was readily broken by the addition of sodium chloride.

In Examples 9 and 10 the water washing of the organic phase is omitted, this phase being merely neutralised with sodium hydroxide solution. In these same two Examples all the reactants are mixed together at the ambient temperature (about 20° C.) and then heated to the reaction temperature; the heating up period is included in the total reaction time.

COMMENTS

Comparative Example 1(b) demonstrates the 5-fold increase in the reaction time when the surfactant is omitted from the process described in Example 1(a). Comparative Example 1(c) demonstrates that there is a similar increase in the reaction time if the cationic surfactant used in Example 1(a) is replaced by a typical anionic surfactant with related structural features. Example 4 demonstrates that there is no significant difference in reaction rate when the cationic surfactant is replaced by a protonatable non-ionic surfactant. The use of this particular non-ionic surfactant does however appear to adversely affect the disengagement of the organic and acid phases at the end of the reaction. This can lead to difficulty with the recovery of OBT and some loss in yield although phase disengagement can be promoted by the addition of sodium chloride.

Comparative Example 6(b) is typical of the conditions recommended in the BASF patent mentioned hereinbefore and Comparative Example 7(b) is typical of the conditions recommended in the Toyama patent specifications. Comparative Example 7(c) demonstrates that the use of 86% orthophosphoric acid in place of 86% sulphuric acid is extremely detrimental both to the rate of reaction and the yield of OBT.

The agitation used was not high shear and in the small scale experiments the rate of agitation was about 500 revolutions per minute. In the large scale experiments the agitation rate was not measured but only a slight vortex was formed indicating that the input of shear energy was low. Furthermore all comparative experiments under each Example number are performed under the same conditions as those illustrating the invention.

| Example | 2-CMT Type | 2-CMT Amount gram-moles | Benzene Amount gram moles | Benzene ratio[1] | Acid | Quantity of Acid gram moles | Quantity of Acid ratio[1] | Surfactant[2] | Quantity Surfactant %[1] (by weight) | Reaction Temp. °C | Time (hours) of Addition | Time (hours) of Reaction | Yield OBT %[1] |
|---|---|---|---|---|---|---|---|---|---|---|---|---|---|
| 1(a) | Invention | 0.2 | 2 | 10:1 | 86% $H_2SO_4$ | 0.5 | 2.5:1 | CTAB | 5.7 | 75 | — | 0.5 | 86 |
| 1(b) | Comparative | 0.2 | 2 | 10:1 | 86% $H_2SO_4$ | 0.5 | 2.5:1 | None | — | 75 | — | 2.5 | 87 |
| 1(c) | " | 0.2 | 2 | 10:1 | 86% $H_2SO_4$ | 0.5 | 2.5:1 | SD | — | 75 | — | 2.5 | 87 |
| 2 | Invention | 0.2 | 2 | 10:1 | 86% $H_2SO_4$ | 0.5 | 2.5:1 | TAB | 5.7 | 75 | — | 2.0 | 88 |
| 3 | " | 0.2 | 2 | 10:1 | 86% $H_2SO_4$ | 0.5 | 2.5:1 | CPB | 5.7 | 75 | — | 0.5 | 90 |
| 4 | " | 0.2 | 2 | 10:1 | 86% $H_2SO_4$ | 0.5 | 2.5:1 | NPE | 5.7 | 75 | — | 0.5 | 80 |
| 5 | " | 2.3 | 15.8 | 7:1 | 86% $H_2SO_4$ | 3.4 | 1.5:1 | CTAB | 2 | 75 | 0.25 | 0.75 | 87 |
| 6(a) | " | 1.7 | 10.6 | 6:1 | 76% $H_2SO_4$ | 9.7 | 5.7:1 | CTAB | 2.5 | 80 | 0.5 | 2.0 | 84 |
| 6(b) | Comparative | 1.5 | 8.9 | 6:1 | 80% $H_2SO_4$ | 8.6 | 5.7:1 | None | — | 80 | 1 | 5 | 84 |
| 7(a) | Invention | 1.4 | 16.9 | 12:1 | 86% $H_2SO_4$ | 2.7 | 2:1 | CTAB | 6.7 | 75 | 1 | 1 | 83 |
| 7(b) | Comparative | 1.4 | 16.9 | 12:1 | 86% $H_2SO_4$ | 2.7 | 2:1 | None | — | 75 | 0.25 | 4 | 85 |
| 7(c) | " | 1.0 | 13.5 | 13.5:1 | 86% $H_3PO_4$ | 3.1 | 3.1:1 | CTAB | 3 | 80 | — | 11 | 10 |
| 8 | Invention | 2.9 | 28.5 | 10:1 | 80% $H_2SO_4$ | 2.9 | 1:1 | CTAB | 1.2 | 75 | 0.5 | 1 | 85 |
| 9 | " | 1.0 | 10.0 | 10:1 | 96% $H_2SO_4$ | 2 | 2:1 | CTAB | 1 | 20 50 | — | 2 0.25 | 70 |
| 10 | " | 75 | 845 | 11:1 | 86% $H_2SO_4$ | 160 | 2:1 | CTAB | 1 | 75 | — | 1.5 | 87 |
| 11 | " | 80 | 930 | 11.5:1 | 86% $H_2SO_4$ | 120 | 1.5:1 | CTAB | 0.5 | 75 | — | 2.0 | 84 |

| Example | α-Chloromethyl benzene Identity | α-Chloromethyl benzene amount g. moles | Benzene Amount gram moles | Benzene ratio[1] | Acid | Quantity of Acid gram moles | Quantity of Acid ratio[1] | Surfactant[2] | Quantity Surfactant %[1] (by weight) | Reaction Temp. °C | Time (hours) of Addition | Time (hours) of Reaction | Yield OBT %[1] |
|---|---|---|---|---|---|---|---|---|---|---|---|---|---|
| 12 | Benzyl chloride | 0.2 | 2 | 10:1 | 86% $H_2SO_4$ | 0.5 | 2.5:1 | CTAB | 4 | 78 | — | 1 | 85 |
| 13 | α-chloro-4-xylene | 0.2 | 2 | 10:1 | 86% $H_2SO_4$ | 0.5 | 2.5:1 | CTAB | 4 | 75 | — | 0.5 | 82 |

NOTES
[1] Relative to 2-CMT
[2] Surfactant identities:
CTAB = cetyltrimethylammonium bromide
SD = sodium dodecyl benzene sulphonate (sodium dobanate)
TAB = tetramethylammonium bisulphate
CPB = cetylpyridinium bromide
NPE = a nonyl phenol ethoxylate having the following structure:

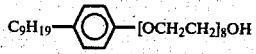

I claim:

1. A process for the preparation of a diphenylmethane by reaction of a benzene with an α-chloromethylbenzene in the presence of sulphuric acid and a cationic surfactant or a non-ionic surfactant which is susceptible to protonation under strong acid conditions.

2. A process according to claim 1 wherein the surfactant carries a long alkyl aliphatic chain containing from 8 to 25 carbon atoms.

3. A process according to claim 1 wherein the surfactant is an alkylammonium salt or a poly-alkoxylated alkylphenol.

4. A process according to claim 1 wherein the catalyst is selected from the group containing cetyltrimethylammonium salts, cetylpyridinium salts and polyalkoxylated nonyl- and octyl-phenols.

5. A process according to claim 1 wherein the surfactant is a phase transfer catalyst.

6. A process according to claim 1 wherein the amount of surfactant is from 0.5% to 2.5% by weight based on the weight of the α-chloromethylbenzene.

7. A process according to claim 1 wherein the strength of the sulphuric acid is from 80% to 95%.

8. A process according to claim 1 wherein the molar ratio of sulphuric acid to the α-chloromethylbenzene is from 1:1 to 6:1.

9. A process according to claim 1 wherein the molar ratio of the benzene to the α-chloromethyl benzene is from 5:1 to 15:1.

10. A process according to claim 1 where the benzene is unsubstituted and the α-chloromethyl benzene is α-chloromethylbenzene, 2-chloromethyl toluene or 4-chloromethyltoluene.

* * * * *